(12) United States Patent
Weinberg et al.

(10) Patent No.: US 11,378,632 B2
(45) Date of Patent: Jul. 5, 2022

(54) APPARATUS AND METHOD FOR RAPID AND COMFORTABLE MAGNETIC IMAGING OF BREAST TISSUES, WITH CULTURAL SENSITIVITY

(71) Applicant: Weinberg Medical Physics, Inc., North Bethesda, MD (US)

(72) Inventors: Irving N. Weinberg, Bethesda, MD (US); Aleksandar Nelson Nacev, Bethesda, MD (US)

(73) Assignee: Weinberg Medical Physics Inc.

( * ) Notice: Subject to any disclaimer, the term of this patent is extended or adjusted under 35 U.S.C. 154(b) by 358 days.

(21) Appl. No.: 15/431,180

(22) Filed: Feb. 13, 2017

(65) Prior Publication Data

US 2017/0234946 A1 Aug. 17, 2017

Related U.S. Application Data

(60) Provisional application No. 62/296,344, filed on Feb. 17, 2016.

(51) Int. Cl.
| | |
|---|---|
| *G01R 33/3415* | (2006.01) |
| *G01R 33/381* | (2006.01) |
| *G01R 33/28* | (2006.01) |
| *G01R 33/38* | (2006.01) |
| *A61B 5/055* | (2006.01) |
| *G01R 33/30* | (2006.01) |
| *A61B 5/00* | (2006.01) |

(52) U.S. Cl.
CPC .......... *G01R 33/3415* (2013.01); *A61B 5/004* (2013.01); *A61B 5/055* (2013.01); *A61B 5/708* (2013.01); *G01R 33/288* (2013.01); *G01R 33/381* (2013.01); *G01R 33/3806* (2013.01); *G01R 33/3808* (2013.01)

(58) Field of Classification Search
CPC ....... A61B 5/004; A61B 5/0555; A61B 5/708; G01R 33/288; G01R 33/3415; G01R 33/3806; G01R 33/3808; G01R 33/381
See application file for complete search history.

(56) References Cited

U.S. PATENT DOCUMENTS

| | | | |
|---|---|---|---|
| 5,003,979 | A | 4/1991 | Merickel et al. |
| 5,252,924 | A | 10/1993 | Sakurai et al. |
| 7,970,452 | B2 | 6/2011 | Piron |
| | | (Continued) | |

OTHER PUBLICATIONS

Weinberg et al.; "Method and Apparatus for Manipulating Electro-Permanent Magnets for Magnetic Resonance Imaging and Image Guided Therapy"; U.S. Appl. No. 62/292,945.
(Continued)

*Primary Examiner* — Michael T Rozanski
(74) *Attorney, Agent, or Firm* — Barnes & Thornburg LLP

(57) ABSTRACT

Disclosed embodiments provide an apparatus and method for imaging breast tissue of a subject, wherein a subject is positioned on a structure so that at least a portion of the subject's body is supported by the structure, magnetic resonance imaging is performed on the portion of the subject's body using an MRI system including a plurality of MRI coils positioned in proximity to the structure, wherein, while the portion of the subject's body is positioned upon the structure, breast tissue of the subject's body is compressed in the proximity of plurality of MRI coils.

13 Claims, 2 Drawing Sheets

(56) References Cited

U.S. PATENT DOCUMENTS

| | | |
|---|---|---|
| 8,154,286 B2 | 4/2012 | Weinberg |
| 8,836,329 B2 | 9/2014 | Weinberg |
| 2004/0151358 A1 | 8/2004 | Yanagita et al. |
| 2006/0084857 A1 | 4/2006 | Massengill et al. |
| 2011/0004093 A1 | 1/2011 | Roscher |
| 2011/0044524 A1 | 2/2011 | Wang et al. |
| 2012/0010497 A1 | 1/2012 | Ehman et al. |
| 2013/0046169 A1* | 2/2013 | Weinberg ................ A61N 2/02 600/411 |

OTHER PUBLICATIONS

Nacev: "Method and Apparatus for High Slew Rate Single Point Magnetic Resonance Maging of Magnetizable Nanoparticles"; U.S. Appl. No. 62/255,843.

* cited by examiner

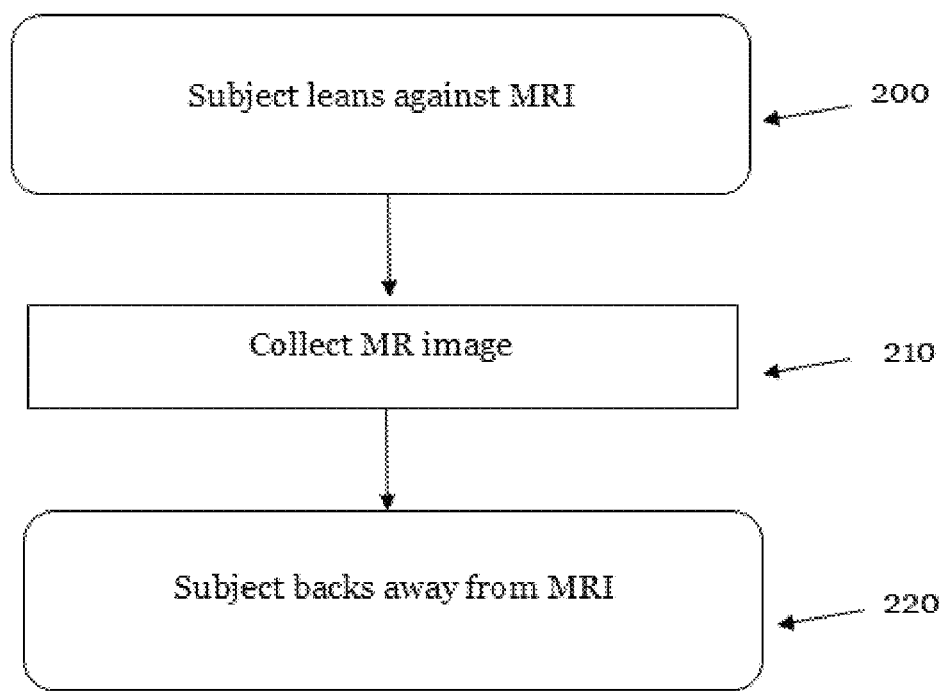

APPARATUS AND METHOD FOR RAPID AND COMFORTABLE MAGNETIC IMAGING OF BREAST TISSUES, WITH CULTURAL SENSITIVITY

CROSS REFERENCE AND PRIORITY CLAIMS

This patent application claims priority to U.S. Provisional Application Provisional Patent Application No. Patent Application Ser. No. 62/296,344, entitled "APPARATUS AND METHOD FOR RAPID COMFORTABLE MAGNETIC IMAGING OF BREAST TISSUES, WITH CULTURAL SENSITIVITY," filed Feb. 17, 2016, the disclosure of which being incorporated herein by reference in its entirety.

FIELD OF USE

Disclosed embodiments provide a method and apparatus for clinical imaging of human tissue, in particular breast tissue.

BACKGROUND

Conventional breast imaging systems have been used to detect and characterize breast lesions. Such systems use various imaging modalities including those based on x-rays, ultrasound, Magnetic Resonance Imaging (MRI), and visible and infrared light.

SUMMARY

Disclosed embodiments provide an apparatus and method for imaging breast tissue of a subject, wherein a subject is positioned on a structure so that at least a portion of the subject's body is supported by the structure, magnetic resonance imaging is performed on the portion of the subject's body using an MRI system including a plurality of MRI coils positioned in proximity to the structure, wherein, while the portion of the subject's body is positioned upon the structure, breast tissue of the subject's body is compressed in the proximity of plurality of MRI coils.

BRIEF DESCRIPTION OF THE FIGURES

The detailed description particularly refers to the accompanying figures in which:

FIG. 2 shows a flow chart describing operation of the apparatus and method.

DETAILED DESCRIPTION OF THE DISCLOSED EMBODIMENTS

Figure 1:
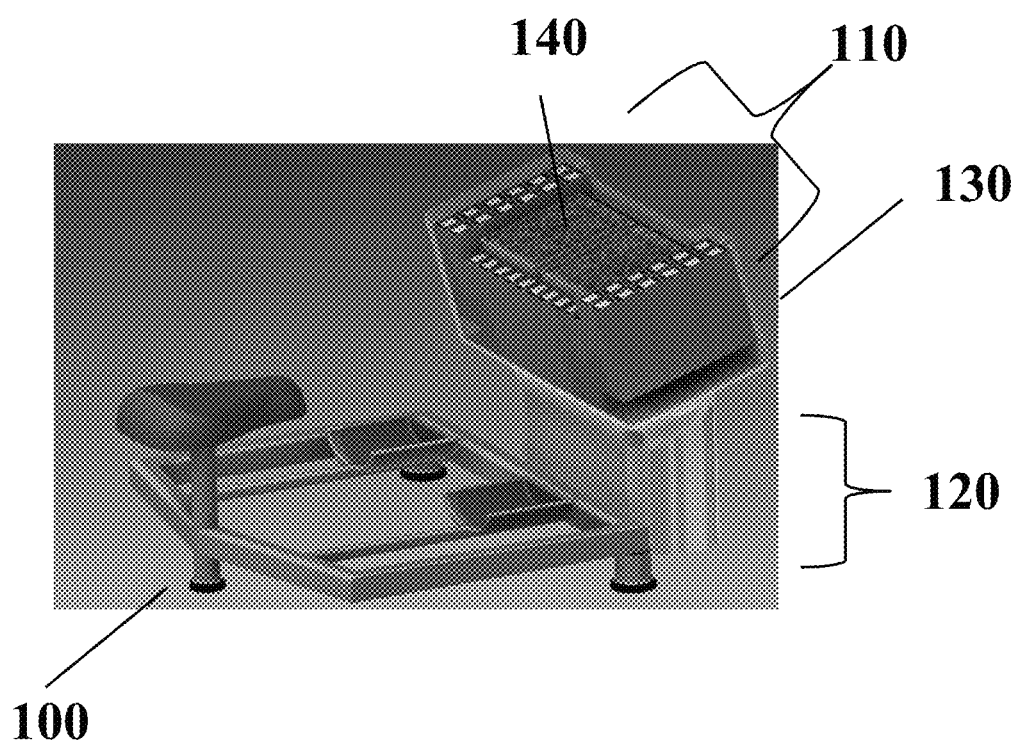
FIG. 1 shows an embodiment of the apparatus, comprising a chair or other support 100 for a person to sit upon, and an MRI system 110 upon which the person may place her or his breast tissues.

FIG. 1 shows an embodiment of the apparatus comprising a chair or other support 100 for a person to sit upon, and an MRI system 110 upon which the person may place her or his breast tissues. For the purpose of the disclosed embodiments, the term MRI system comprises components used to form an image using magnetic resonance or magnetic particle imaging. The MRI system 110 comprises subunits 130 and 140, where 130 includes coils or magnets (or electro-permanent magnets) that polarize protons or other nuclei or electrons in the breast tissues, and where 140 includes gradient and/or radiofrequency coils to form an image. Support structure 120 may hold the MRI system and may contain other components needed to operate or move the MRI system, for example wheels and/or batteries. The display system is not shown in the figure, but is understood to be present in order to view images.

FIG. 2 shows a flow chart describing operation of the apparatus and method. Subject leans against the MRI system 110 to initiate the process 200. Images are collected 210, and then the subject moves away from the MRI 220.

Disclosed embodiments comprise an apparatus and method for imaging the mammalian breast. In accordance with at least one embodiment, a person (typically female) sits upon a patient support structure 100 and, with the assistance of gravity places her breast tissues upon an MRI system 110, thereby partially compressing the breast tissues. Compression may be helpful in a single-sided MRI, because in a single-sided MRI, the usable field-of-view does not typically extend throughout the patient's body, but only extends a small distance (for example, 15 cm) from the edge of the MRI system. Typically, the act of sitting would be with bent knees; however, alternative structural configurations to assist a subject's comfort may be provided to facilitate positioning of the subject and breast tissues.

It is understood that the term "her" may refer to a male or female person, and the term breast may refer to a male breast (as a result of gynecomastia), or to a female breast including artificial markers or fillers.

It should be understood that, in accordance with disclosed embodiments, images of breast tissues may be obtained for the breast piecewise, that is by imaging one or more sections of the breast at a time, since it is often difficult in a single-sided MRI to obtain very good uniformity over the entire breast. Such sectional images can be assembled into an image of the entire breast with software. It is understood that the spatial resolution of certain portions of breast tissues may be different than in other portions, depending on the gradient applied at the time of image acquisition, which may be useful in order to better characterize certain regions of breast tissues.

In accordance with at least one embodiment, it is not necessary for the subject to disrobe, since the MRI signal from the breast tissues is not substantially affected by the presence of thin layers of clothing between the breast tissues and the MRI. This lack of requirement to disrobe has particular technical utility that is not usually found in other breast imaging modalities, and is useful in populations where there are cultural prohibitions against removal of clothing under certain circumstances.

In accordance with at least one embodiment, the MRI system 110 may be suspended or otherwise attached to a platform 120, which may contain electronics or batteries or wheels or other material. It is to be understood that the patient support structure 100 and/or the MRI support structure 120 may have parts that are adjustable in order to accommodate patients of different heights and sizes.

The MRI system 110 may be a single-sided MRI (as depicted in FIG. 1), or may be a 3-sided system, so long as the person may rest her chest against a portion of the system 110. The portion of the MRI system 110 comprises subunits 130 and 140 that are used to form the MR image. Subunit 130 may comprise electrical coils and/or electro-permanent magnets, in which said electro-permanent magnets that are magnetized by a transient current flowing through electrical coils and stay activated until the magnetization is removed by other transient currents flowing through electrical coils. Subunit 140 comprises radiofrequency, gradient, pre-polarizing and/or shimming coils that may be needed to form an image. Subunit 130 coils may also have a role to play as gradient and shim coils. It is to be understood that a waterproof material or another housing material to prevent user interference may cover the MRI system 110 and/or its subunits.

In an embodiment, ultra-fast and high-magnitude gradient pulses as described by Irving Weinberg in U.S. Pat. No. 8,154,286, entitled "APPARATUS AND METHOD FOR DECREASING BIO-EFFECTS OF MAGNETIC FIELDS," and related patents and patent applications (related by priority claims), all being incorporated by reference, may be used to collect many sets of data points in order to achieve high spatial resolution and signal-to-noise ratio, without causing uncomfortable nerve stimulation. As taught in U.S. Pat. No. 8,154,286, the MRI could employ a gradient transition time of 10 microseconds or less, which is less than the neurological response time for neurological tissue. The slew rate (that is, the change of magnetic field per distance per time) is increased as a result of the reduced pulse ramp times. The plateau magnitude of the magnetic gradient pulse is increased, as compared to the prior art, because of several factors. Firstly, the plateau magnitude may be increased because of the improved switching techniques as described above. Secondly, the plateau magnitude may be increased because the tissues are depolarized and repolarized within a short period of time similar to the neurological response time. As discussed in U.S. Pat. No. 8,154,286, the magnitude of the gradient pulse may be as high as 1000 T/m.

Such high magnetic gradient field magnitude may be 400 mT or higher, with rise-times of 10 microseconds or less. The gradient pulses may be so rapid as to permit acquisition in a very short time, for example 10 seconds or less, so that there is little motion of the breast during acquisition, thereby reducing resolution loss from "motion-unsharpness."

In accordance with at least one embodiment, pre-polarizing coils may be activated in order to improve signal-to-noise ratio, as taught in U.S. Pat. No. 8,836,329 by Weinberg, entitled "ULTRA-FAST PRE-POLARIZING MAGNETIC RESONANCE IMAGING AND SYSTEM" (incorporated by reference). As taught in U.S. Pat. No. 8,836,329, a pre-polarizing magnetic pulse may be applied to a structure of interest, in which the magnetic pulse has a rise-time of less than 10 microseconds and a fall time of less than 10 microseconds, or the magnetic pulse following a pre-polarizing magnetic pulse has a rise-time of less than 10 microseconds and a fall time of less than 10 microseconds. As recited in U.S. Pat. No. 8,836,329, it is conventionally known that application of a high transient magnetic field during the polarization portion of the pulse sequence results in an improved signal (see for example, A Macovski, S Conolly: "NOVEL APPROACHES TO LOW-COST MRI", in Magnetic Resonance in Medicine 30:221-230, the subject matter of which is incorporated herein by reference in its entirety) because more spins are aligned; as a result, the application of this field subsequently results in output of a more significant signal as they return to their equilibrium state.

In accordance with at least one embodiment, electropermanent magnets may be deactivated in the case of nearby ferromagnetic materials, as taught in U.S. Provisional Patent Application No. 62/292,945 (now filed as a U.S. patent application Ser. No. 15/427,426) by Weinberg and Nacev, entitled "METHOD AND APPARATUS FOR MANIPULATING ELECTRO-PERMANENT MAGNETS FOR MAGNETIC RESONANCE IMAGING AND IMAGE GUIDED THERAPY" (incorporated by reference). As taught in that application, a soft magnetic material can be in close proximity to an additional soft magnetic material and a hard magnetic material and a conductive material to form one or more electropermanent arrays. Conductive material near the soft magnetic material may be energized with current, so that magnetic component from the one or more electropermanent arrays will be magnetized in a direction and/or magnitude, which may be selected by a user (via controlling equipment) or automated algorithm by a computer (that provides an automated or semi-automated controller). The magnetic field produced by one or more electropermanent arrays can be reduced or increased by adjusting the magnetization of one or more electropermanent arrays. In an embodiment, the ultra-fast gradient pulses may be used to effectively visualize and/or segment small calcifications in the breast tissues, which is generally not possible with MRI because the pulse sequences of MRI are too slow to catch the rapidly decaying signals from solid-bound water near calcifications. This method is similar to that described by Nacev in U.S. Provisional Patent Application No. 62/255,843 (and now filed as U.S. patent application Ser. No. 15/352,164) entitled "METHOD AND APPARATUS FOR HIGH SLEW RATE SINGLE POINT MAGNETIC RESONANCE IMAGING OF MAGNETIZABLE NANOPARTICLES" (incorporated by reference). As taught in those patent applications, magnetic gradient pulses are applied with very short durations (for example, between 10 and 200 microseconds), and/or switched on and/or off quickly (for example, between 10 and 100 microseconds). The quickly actuated short gradient pulses (see 330 and 340) allow for polarized species to be imaged very quickly after an RF excitation pulse (e.g. with very short TE times). The rapid decay of signals from protons in the region of microcalcifications may be employed to segment the microcalcifications, thereby aiding in diagnosis.

In accordance with at least one embodiment, the apparatus may be lightweight enough to be transported on wheels and may take such little power to operate that it may be operated in remote locations using batteries or small generators.

The magnetic field from electropermanent magnets may be rapidly reduced through application of electrical currents, which would be useful in the case of ferromagnetic objects being attracted to the electropermanent magnet. In accordance with at least one embodiment, such rapid reduction would be actuated by a technologist. In an embodiment, said reduction could be performed automatically by a computer that detecting the presence of ferromagnetic objects approaching the apparatus. Said detection could include a change in the radio-frequency signals collected by the apparatus. An example of such safety feature was described in the U.S. patent application Ser. No. 15/427,426 (as discussed above) by Weinberg entitled "METHOD AND APPARATUS FOR USING ELECTROPERMANENT MAGNETS FOR MAGNETIC RESONANCE IMAGING AND IMAGE-GUIDED THERAPY" (incorporated by reference).

In accordance with at least one embodiment, the pixel size for images obtained with the apparatus may be less than 50 microns, as taught by Nacev and others in the 2014 ISMRM publication entitled "A quiet, fast, high-resolution desktop MRI capable of imaging solid-bound water" (incorporated by reference).

In at least one embodiment, fast MRI pulse sequences are used to image calcium-rich structures, such as microcalcifications that often accompany breast cancers. The use of such pulse sequences without unpleasant nerve stimulation are described in the U.S. patent application Ser. No. 15/352, 164 by Nacev entitled "METHOD AND APPARATUS FOR HIGH SLEW RATE SINGLE POINT MAGNETIC RESONANCE IMAGING OF MAGNETIZABLE NANOPARTICLES" (as discussed above and incorporated by reference). Conventional MRI systems obtain low signals from such structures.

In accordance with at least one embodiment, the pixel size may be less than 20 microns.

In accordance with at least one embodiment, the spatial resolution and pixel size is sufficient to perform MRI histology, in which the internal features of cells (for example, nuclear to cytoplasm ratio) may be observed in order to characterize whether the cell is malignant or not. It should be understood that the MR images obtained with the apparatus may be employed in order to guide a biopsy or other intervention. Examples of such interventions may include destruction of tumor cells via radiofrequency deposition, or via heating or motion of small magnetic particles introduced into the body intravenously or some other means.

It should be understood that the MRI examination obtained with the presently disclosed apparatus may be performed with contrast administered and/or may employ diffusion-weighted or other imaging methods to detect and characterize breast lesions. It should be understood that the images may be used to guide biopsy, potentially through correlation with other imaging modalities such as ultrasound. It should also be understood that an ultrasound transducer may be incorporated into MRI system 110 so as to collect co-registered MRI and ultrasound images.

In accordance with at least one embodiment, images of one or both breasts may be obtained in a single session with the system.

In accordance with at least one embodiment, one or more coils or electro-permanent magnets within the MRI system may be fabricated with additive manufacturing, as taught by Urdaneta et al in the 2011 IEEE Medical Imaging Proceedings entitled "Good-bye Wires and Formers: 3-D Additive Manufacturing and Fractal Cooling Applied to Gradient Coils".

In accordance with at least one embodiment, the subject may pull herself towards the MRI system by using her arms to grab a projection from the apparatus.

For the purposes of this disclosure, the term "external pressure" is intended to mean any force applied to any portion of the subject other than gravity or the subject's own exertions. As an example, a subject may lean against the apparatus, using the force of gravity to compress one or more portions of a breast against one or more surfaces of the apparatus. In an alternative embodiment, the subject may use her arms to grasp a projection as to compress one or more portions of breast against one or more surfaces of the apparatus.

It is understood that the invention may be applied to both men and women. In the case of men, the technical utility of the disclosed embodiments may be particularly useful to provide good options for breast examination of men.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments of, as set forth above, are intended to be illustrative, not limiting. Various changes may be made without departing from the spirit and scope of the invention.

The invention claimed is:

1. An apparatus for imaging breast tissue of a subject, the apparatus comprising:
structure upon which at least a portion of the subject's body is positioned;
a magnetic resonance imaging system including a plurality of electro-permanent magnets positioned in a proximity of within 15 cm to the structure,
wherein, while the portion of the subject's body is positioned upon the structure, breast tissue of the subject's body is compressed in the proximity of at least one of the electro-permanent magnets with no external pressure applied, the MRI system is configured to control an amount of remanent magnetization of the electro-permanent magnets and image at least one microcalcification in the breast tissue,
wherein the magnetic resonance imaging system is single-sided, and
wherein the structure is further configured to accommodate the subject positioned seated upon the structure with bended knees during the imaging while the breast tissue is compressed on the structure.

2. The apparatus of claim 1, wherein magnetic gradient pulses are generated to segment signals from the at least one microcalcification within the breast tissue.

3. The apparatus of claim 1, wherein the pixel size of images obtained with the apparatus is less than 50 microns.

4. The apparatus of claim 1, wherein the apparatus is configured to image the subject when a fabric is present between the breast tissue and the MRI system.

5. The apparatus of claim 1, wherein the electro-permanent magnets are rapidly demagnetized in the case of nearby ferromagnetic materials as detected by the MRI system.

6. The apparatus of claim 1, wherein the magnetic resonance imaging system generates magnetic gradient pulses with rise or fall-times that are less than 10 microseconds.

7. A method for imaging breast tissue of a subject, the method comprising:
positioning at least a portion of the subject's body on a structure to compress the portion of the subject's body on the structure via gravity with no external pressure applied;
imaging at least one microcalcification in breast tissue of the subject's body using a magnetic resonance imaging system including a plurality of electro-permanent magnets, the MRI system configured to control an amount of remanent magnetization of the electro-permanent magnets,
wherein at least one of the electro-permanent magnets is positioned in a proximity of within 15 cm to the structure,
wherein the magnetic resonance imaging system is single-sided, and
wherein the subject's knees are bent and the subject is seated during the imaging while the breast tissue is compressed on the structure.

8. The method of claim 7, wherein the pixel size of images obtained by the imaging is less than 50 microns.

9. The method of claim 7, wherein an examination is completed in 10 seconds or less.

10. The method of claim 7, wherein the subject wears clothing positioned between the breast tissue and the MRI system during an examination with the MRI system.

11. The method of claim 7, wherein a static magnetic field is rapidly diminished in the case where nearby ferromagnetic materials are detected by the MRI system.

12. The method of claim 7, wherein the magnetic resonance imaging system generates magnetic gradient pulses with rise or fall-times that are less than 10 microseconds.

13. The method of claim 7, wherein the imaging the at least one microcalcification comprises segmentation of the at least one microcalcification.

\* \* \* \* \*